US007494652B1

(12) United States Patent
Kink

(10) Patent No.: US 7,494,652 B1
(45) Date of Patent: Feb. 24, 2009

(54) TREATMENT OF SEPSIS

(75) Inventor: John A. Kink, Madison, WI (US)

(73) Assignee: Promega Corporation, Madison, WI (US)

(*) Notice: Subject to any disclaimer, the term of this patent is extended or adjusted under 35 U.S.C. 154(b) by 0 days.

(21) Appl. No.: 09/095,536

(22) Filed: Jun. 10, 1998

(51) Int. Cl.
*A61K 39/395* (2006.01)
*C07K 16/00* (2006.01)

(52) U.S. Cl. .................. 424/158.1; 530/389.2
(58) Field of Classification Search .............. 424/130, 424/145.1, 157.1, 139.1, 810, 436, 435, 464, 424/158.1; 530/387.1, 388.23, 389.1, 389.2, 530/853, 861, 388.2

See application file for complete search history.

(56) References Cited

U.S. PATENT DOCUMENTS

| 4,870,163 | A | | 9/1989 | Rubin et al. ................ 530/413 |
| 5,385,901 | A | | 1/1995 | Kaplan et al. ............ 514/231.5 |
| 5,420,253 | A | * | 5/1995 | Emery et al. ................ 530/423 |
| 5,436,154 | A | | 7/1995 | Barbanti et al. ......... 435/240.27 |
| 5,585,098 | A | * | 12/1996 | Coleman et al. ........... 424/157.1 |
| 5,591,827 | A | * | 1/1997 | Brakenhoff et al. .......... 530/351 |
| 5,654,407 | A | | 8/1997 | Boyle et al. ............. 530/338.15 |
| 5,656,272 | A | | 8/1997 | Le et al. ................... 424/133.1 |
| 5,723,120 | A | * | 3/1998 | Brakenhoff et al. ......... 424/85.2 |
| 5,747,532 | A | * | 5/1998 | Lai ............................ 514/491 |
| 5,888,511 | A | * | 3/1999 | Skurkovich et al. ....... 424/145.1 |

FOREIGN PATENT DOCUMENTS

| WO | WO 9108774 | * | 6/1991 |
| WO | WO 96/33204 | | 10/1996 |
| WO | WO 9814209 | * | 4/1998 |
| WO | WO 9814209 A1 | * | 4/1998 |

OTHER PUBLICATIONS

Starnes et al. Anti-IL-6 monoclonal antibodies protect against lethal *E. coli* infection and lethal TNF-alpha challenge in mice, Juornal of Immunology, vol. 145, No. 12, pp. 4185-4191, Dec. 1990.*
Doherty et al. Evidence for IFN-gamma as a mediator of the lethality of endotoxin and TNF alpha, Journal of Immunology, vol. 149, No. 5, pp. 1666-1670, Sep. 1992.*
Beutler B. et al. Science 299;869-871 Aug. 30, 1985.*
WebMD listing of symptoms of AIDS: http://www.webmd.com/hw/hiv_aids/hw151445.asp.*
Machiedo et al., "Patterns of Mortality in a Surgical Intensive Care Unit," *Surg. Gyn. & Obstet.* 152:757-759 (1981).
Morris et al., "Endotoxemia in neonatal calves given antiserum to a mutant *Escherichia coli* (J-5)," *Am. J. Vet. Res.* 47:2554-2565 (1986).
Hoffman et al., "Prognostic Variables for Survival of Neonatal Foals Under Intensive Care," *J. Vet. Int. Med.* 6:89-95 (1992).
Wolff, "Monoclonal Antibodies and the Treatment of Gram-Negative Bacteremia and Shock," *New Eng. J. Med.* 324:486-488 (1991).

K.A. Schulman et al., "Cost-effectiveness of HA-1A Monoclonal Antibody for Gram-Negative Sepsis," *JAMA* 266:3466-3471 (1991).
K. Ohlsson et al., "Interleukin-1 receptor antagonist reduces mortality from endotoxin shock," *Nature* 348:550-552 (1990).
R.C. Bone, "The Pathogenesis of Sepsis," *Ann. Intern. Med.* 115:457-469 (1991).
K.J. Tracey et al., "Shock and Tissue Injury Induced by Recombinant Human Cachectin," *Science* 234:470-474 (1986).
A. Tewari et al., "Preliminary report: effects of interleukin-1 on platelet counts," *Lancet* 336:712-714 (1990).
S.M. Opal et al., "Efficacy of a Monoclonal Antibody Directed against Tumor Necrosis Factor in Protecting Neutropenic Rats from Lethal Infection with *Pseudomonas aeruginosa*," *J. Infect. Dis.* 161:1148-1152 (1990).
Polson et al., "Antibodies to Proteins from Yolk of Immunized Hens," *Immunol. Comm.*, 9:495 (1980).
C. Galanos et al., "Galactosamine-induced sensitization to the lethal effects of endotoxin," *Proc. Natl. Acad. Sci. USA* 76:5939-5943 (1979).
J. Rothe et al. "Mice lacking the tumor necrosis factor receptor 1 are resistant to TNF-mediated toxicity but highly susceptible to infection by Listeria monocytogenes," *Nature* 364:798-802 (1993).
S.Q. DeJoy et al., "Effect of CL 184,005, a Platelet-Activating Factor Antagonist in a Murine Model of *Staphylococcus auteus*-Induced Gram-Positive Sepsis," *J. Infect. Dis.* 169:150-156 (1994).
Opal et al., "Potential Hazards of Combination Immunotherapy in the Treatment of Experimental Septic Shock," *J. of Infectious Diseases* 173:1415-1421 (1996).
Russell et al., "Combined Inhibition of Interleukin-1 and Tumor Necrosis Factor in Rodent Endotoxemia: Improved Survival and Organ Function," *J. of Infectious Diseases* 171:1528-1538 (1995).
Plevy et al., "A Role for TNF-α and Mucosal T Helper-1 Cytokines in the Pathogenesis of Crohn's Disease," *J. of Immunology* 159:6277-6282 (1997).
Van Dullemen et al., "Treatment of Crohn's Disease With Anti-Tumor Necrosis Factor Chimeric Monoclonal Antibody (cA2)," *Gastroenterology* 109:129-138 (1995).
Targan et al., "A Short-Term Study of Chimeric Monoclonal Antibody cA2 to Tumor Necrosis Factor α for Crohn's Disease," *NEJM*, 337:1029-1035 (1997).
Elliott et al., "Randomised double-blind comparison of chimeric monoclonal antibody to tumor necrosis factor α (cA2) versus placebo in rheumatoid arthritis," *Lancet* 344:1105-1110 (1994).
Elliott et al., "Repeated therapy with monoclonal antibody to tumor necrosis factor α (cA2) in patients with rheumatoid arthritis," *Lancet* 344:1125-1127 (1994).
Kojouharoff et al., "Neutralization of tumor necrosis factor (TNF) but not of IL-1 reduces inflammation in chronic dextran sulphate sodium-induced colitis in mice," *Clin Exp Immunol* 107:353-358 (1997).
Olson et al., "Antiserum to Tumor Necrosis Factor and Failure to Prevent Murine Colitis," *J Ped Gastroenterology Nutrition* 21:410-418 (1995).
Zacharchuk et al., "Macrophage-mediated cytotoxicity: Role of a soluble macrophage cytotoxic factor similar to lymphotoxin and tumor necrosis factor," *PNAS USA* 80:6341-6345 (1983).

*Primary Examiner*—Robert S. Landsman
*Assistant Examiner*—Bruce D Hissong

(74) *Attorney, Agent, or Firm*—Medlen & Carroll, LLP

(57) ABSTRACT

Compositions and methods are described for treatment of sepsis in animals, including humans. Unique and specific combinations of polyclonal antibodies directed to cytokines are shown to have a beneficial effect in animal models predictive of human therapy.

7 Claims, No Drawings

OTHER PUBLICATIONS

Zacharchuk, Charles Michael, "A Macrophage Cytotoxic Factor: Immunochemical and Functional Characterization," Dissertation Abstract.

Pennica et al., "Human tumor necrosis factor: precursor structure, expression and homology to lymphotoxin," *Nature* 312:724-729 (1984).

Ruff, Michael Roland, "Mechanism of Action of a Serum Oncolytic Protein, Rabbit Tumor Necrosis Factor," Dissertation Abstract.

Doherty et al., "Evidence for IFN-γ as a Mediator of the Lethality of Endotoxin and Tumor Necrosis Factor-α," *J. Immunology* 149(5):1666-1670 (1992).

Manthey et al., "The role of cytokines in host responses to endotoxin," *Reviews in Medical Microbiology* 3(2):72-79 (1992).

Starnes et al., "Anti-IL-6 Monoclonal Antibodies Protect Against Lethal *Escherichia coli* Infection and Lethal Tumor Necrosis Factor-α challenge in mice," J. of Immun. 145(12):4185-4191 (1990).

\* cited by examiner

TREATMENT OF SEPSIS

FIELD OF THE INVENTION

The present invention relates to therapeutics for the prevention and treatment of blood-borne and toxin mediated diseases, and in particular the prevention and treatment of sepsis in humans as well as other animals.

BACKGROUND OF THE INVENTION

Sepsis is a major cause of morbidity and mortality in humans and other animals. It is estimated that 400,000-500,000 episodes of sepsis resulted in 100,000-175,000 human deaths in the U.S. alone in 1991. Sepsis has become the leading cause of death in intensive care units among patients with non-traumatic illnesses. [G. W. Machiedo et al., *Surg. Gyn. & Obstet.* 152:757-759 (1981).] It is also the leading cause of death in young livestock, affecting 7.5-29% of neonatal calves [D. D. Morris et al., *Am. J. Vet. Res.* 47:2554-2565 (1986)], and is a common medical problem in neonatal foals. [A. M. Hoffman et al., *J. Vet. Int. Med* 6:89-95 (1992).] Despite the major advances of the past several decades in the treatment of serious infections, the incidence and mortality due to sepsis continues to rise. [S. M. Wolff, *New Eng. J. Med.* 324:486-488 (1991).]

Sepsis is a systemic reaction characterized by arterial hypotension, metabolic acidosis, decreased systemic vascular resistance, tachypnea and organ dysfunction. Sepsis can result from septicemia (i.e., organisms, their metabolic endproducts or toxins in the blood stream), including bacteremia (i.e., bacteria in the blood), as well as toxemia (i.e., toxins in the blood), including endotoxemia (i.e., endotoxin in the blood). The term "bacteremia" includes occult bacteremia observed in young febrile children with no apparent foci of infection. The term "sepsis" also encompasses fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by a number of organisms.

The systemic invasion of microorganisms presents two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and oftentimes, death.

There are three major types of sepsis characterized by the type of infecting organism. Gram-negative sepsis is the most common and has a case fatality rate of about 35%. The majority of these infections are caused by *Escherichia coli, Klebsiella pneumoniae* and *Pseudomonas aeruginosa*. Gram-positive pathogens such as the staphylococci and streptococci are the second major cause of sepsis. The third major group includes the fungi, with fungal infections causing a relatively small percentage of sepsis cases, but with a high mortality rate.

Many of these infections are acquired in a hospital setting and can result from certain types of surgery (e.g., abdominal procedures), immune suppression due to cancer or transplantation therapy, immune deficiency diseases, and exposure through intravenous catheters. Sepsis is also commonly caused by trauma, difficult newborn deliveries, and intestinal torsion (especially in dogs and horses).

Many patients with septicemia or suspected septicemia exhibit a rapid decline over a 24-48 hour period. Thus, rapid methods of diagnosis and treatment delivery are essential for effective patient care. Unfortunately, a confirmed diagnosis as to the type of infection traditionally requires microbiological analysis involving inoculation of blood cultures, incubation for 18-24 hours, plating the causative organism on solid media, another incubation period, and final identification 1-2 days later. Therefore, therapy must be initiated without any knowledge of the type and species of the pathogen, and with no means of knowing the extent of the infection.

It is widely believed that anti-endotoxin antibody treatment administered after sepsis is established may yield little benefit because these antibodies cannot reverse the inflammatory cascade initiated by endotoxin. In addition, the high cost of each antibody (Centoxin HA-1A was expected to cost $3700 per 100 mg dose) would limit physicians' use of a product where no clear benefit has been demonstrated. [K. A. Schulman et al., *JAMA* 266:3466-3471 (1991).] Of course, these endotoxin antibodies only target gram-negative sepsis; no equivalent antibodies exist for the array of gram-positive organisms and fungi.

With new knowledge regarding the effects of endotoxin on host inflammatory responses, other therapies are being attempted. For example, an IL-1 receptor antagonist has been identified that occupies the same receptor site as IL-1, but mediates no biological effect. Blockage of the IL-1 receptor with this molecule can reduce mortality from endotoxin shock. [K. Ohlsson et al., *Nature* 348:550-552 (1990).] While the IL-1 receptor antagonist appears to be well-tolerated, the required dosage is extremely large (over 100 mg of recombinant protein per kg of body weight is infused over a period of hours to days). For human therapy, the 8-10 grams of recombinant protein anticipated to be required is likely to be extremely costly (several thousand dollars).

Clearly, there is a great need for agents capable of preventing and treating sepsis. It would be desirable if such agents could be administered in a cost-effective fashion. Furthermore, approaches are needed to combat all forms of sepsis, not just gram-negative cases.

SUMMARY OF THE INVENTION

The present invention relates to therapeutics for the prevention and treatment of blood-borne and toxin-mediated diseases, and in particular the prevention and treatment of sepsis in mammals. The present invention relates to compositions and methods for preventing sepsis in high-risk patients, including immunocompromised patients such as surgical and other hospitalized patients, low birth weight infants, and burn and trauma victims. The present invention contemplates treatment of mammals having symptoms of a systemic septic reaction.

In one embodiment, the present invention contemplates a composition comprising a mixture of antibodies directed to TNF and IL-6. In another embodiment, the present invention contemplates a method of relieving symptoms of and rescuing mammals (including humans) from episodes of acute septicemia and septic shock utilizing a combination preparation comprising anti-TNF antibodies and anti-interleukin-6 (IL-6) antibodies. The present invention contemplates a method of treatment, comprising: (a) providing: i) a mammal for treatment, ii) a therapeutic preparation, comprising anti-TNF and anti-IL-6 polyclonal antibodies; and (b) administering said preparation to said mammal (e.g., intravenous or parenterally).

Other combinations of antibodies are also contemplated. For example, in one embodiment, the present invention contemplates the use of antibodies directed to γIFN in combination with other antibodies, such as anti-TNF antibodies.

Preferably, the polyclonal antibody is reactive with TNF across species. Specifically, the present invention demonstrates that immunization with human TNF generates neutralizing antibody capable of reacting with endogenous murine TNF. Thus, the present invention provides anti-TNF antibody that will react with mammalian TNF generally (such as with equine TNF for treatment of equine sepsis).

It is not intended that the present invention be limited to specific preparations of antibodies. However, polyclonal antibodies are preferred. Most importantly, it is preferred that the antibodies not be complement fixing. More specifically, avian antibodies (e.g., chicken antibodies from eggs) are preferred.

The treatment with the combination preparation has the unexpected result of reducing mortality rates in patients when administered within up to four hours of the onset of the acute septicemia/septic shock episode. Clearly, the present invention provides an effective approach to prevention and treatment of sepsis.

While acute treatment is contemplated, the present invention also contemplates a method of treatment of mammals at risk for developing sepsis, in which a therapeutic preparation comprised of a mixture of capable antibodies is administered to the at-risk animal prior to or after the onset of any septic symptoms. In a preferred embodiment, it is contemplated that the method of the present invention will be administered intravenously. The present invention contemplates that the method will be used for such animals as neonatal calves and foals, as well as human and veterinary surgical patients, trauma, and burn victims. It is contemplated that the method will be used to treat immunocompromised patients.

DEFINITIONS

The phrase "symptoms of sepsis" refers to any symptoms characteristic of a subject with sepsis including but not limited to, arterial hypotension, metabolic acidosis, fever, decreased systemic vascular resistance, tachypnea and organ dysfunction. Sepsis can result from septicemia (i.e., organisms, their metabolic end-products or toxins in the blood stream), including bacteremia (i.e., bacteria in the blood), as well as toxemia (i.e., toxins in the blood), including endotoxemia (i.e., endotoxin in the blood). The term "sepsis" also encompasses fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) is a symptom of sepsis.

Such symptoms are subject to quantitative analysis (e.g., fever, etc.). Some symptoms are readily determined from a blood test (e.g., bacteremia). The phrase "wherein said symptoms are reduced" refers to qualitative a or quantitative reduction in detectable symptoms, including but not limited to a detectable impact on the rate of recovery from disease.

The phrase "at risk for sepsis" is herein defined as a subject predisposed to the development of sepsis by virtue of the subject's medical status, including but not limited to such factors as infection, trauma (e.g., abdominal perforation, such as by a gun shot wound), surgery (e.g., intestinal surgery), and invasive procedures (e.g., placement of a catheter, etc.) and the like.

DESCRIPTION OF THE INVENTION

The present invention relates to therapeutics compositions and methods for the prevention treatment of blood-borne and toxin mediated diseases, and in particular the prevention and treatment of sepsis caused by various types of organisms in humans as well as other animals. It is contemplated that the present invention will be used in the treatment of gram-negative and gram-positive sepsis. Although the invention may be used for treatment of sepsis due to one organism, it may also be used to treat sepsis caused by multiple organisms (e.g., sepsis and/or bacteremia due to gram-negative and gram-positive organisms).

As noted above, the present invention also contemplates treatment comprising anti-TNF and anti-IL6 antibody preparations used alone and in combination, as well as other combinations (such as anti-TNF and anti-IFN). The present invention further teaches treatments comprising anti-TNF and anti-IL6 combination preparations and methods used in combination after the onset of symptoms of blood-borne or toxin-mediated diseases. In accordance with the present invention, anti-TNF and anti-IL6 combination preparations are administered intravenously, intra-muscularly, subcutaneously, intradermally, intraperitoneally, intrapleurally, intrathecally or topically.

Importantly, it is not necessary to the successful use of the composition and methods of the present invention that one understand the precise mechanism by which a therapeutic benefit is achieved. However, it is believed that one of the key mediators of septic shock is tumor necrosis factor (TNF). [R. C. Bone, *Ann. Intern. Med.* 115:457-469 (1991).] Indeed, large doses of TNF [K. J. Tracey et al., *Science* 234:470-474 (1986)] and/or IL-1 [A. Tewari et al., *Lancet* 336:712-714 (1990)] can mimic the symptoms and outcome of sepsis.

Monoclonal antibodies have been found to offer some protection in experimental animals [S. M. Opal et al., *J. Infect. Dis.* 161:1148-1152 (1990)] but studies in human patients with sepsis have not been conclusive. The improved results with the combination of antibodies described herein suggest that neutralization of other mediators—along with TNF—is what is needed for a therapeutic benefit.

EXPERIMENTAL

The following examples serve to illustrate certain preferred embodiments and aspects of the present invention and are not to be construed as limiting the scope thereof.

Example 1

Production of Antibodies to Cytokines TNF Alpha, IL-6, Gamma IFN, IL-1B and IL-12 in the Hen This example involved: (a) preparation of the immunogen and immunization; (b) purification of anti-cytokine chicken antibodies from egg yolk (IgY); and (c) detection of anti-cytokine antibodies in the purified IgY preparations.

(a) Preparation of the immunogen and immunization. The cytokines used to immunize the hens were purchased from R&D Systems, Inc., Minneapolis, Minn. and produced in *E. coli*. Specifically what was obtained is as follows: recombinant human Tumor Necrosis Factor Alpha, (TNFα or just TNF), recombinant human Interleukin-6, (IL-6), recombinant mouse Interleukin-1 beta, (IL-1B), recombinant mouse Interferon gamma, (gamma IFN), and recombinant mouse Interleukin-12 p40 homodimer (IL-12). These cytokines were selected because they are all considered pro-inflammatory cytokines released in response to infection. All the above recombinant proteins were purchased lyophilized without bovine serum albumin (BSA) and designated carrier-free. This was done to prevent an interfering antibody response against BSA after immunization. The lyophilized cytokine was reconstituted in phosphate-buffered saline pH 7.2-7.5 (PBS) at 50-100 µg/ml and from 2-10 µg of cytokine was used to immunize each hen. Each hen received one 0.5 ml subcutaneous injection containing cytokine with 75 µg Quil A adjuvant (Superfos Biosector, Denmark, distributed by Accurate Chem., Westbury, N.Y.) in PBS. The hens were immunized every 2 weeks for at least 3 times then placed on a maintenance immunization schedule where the hens were immunized every 4-6 weeks.

(b) Purification of anti-cytokine chicken antibodies from egg yolk (IgY). Groups of eggs were collected per immunization group at least 3-5 days after the last booster immunization. The chicken yolk immunoglobulin (IgY) was extracted by a two-step polyethylene glycol (PEG) 8000 method performed according to a modification of the procedure of Polson et al., *Immunol. Comm.*, 9:495 (1980). The yolks were separated from the whites and the yolks were placed in a graduated cylinder. The pooled yolks were blended with 4 volumes of PBS and PEG was added to a concentration of 3.5%. When the PEG was dissolved, the protein and lipid precipitates that formed were pelleted by centrifugation at 9,000×g for 15 minutes. The supernatants were decanted and filtered through 4 layers of gauze to remove the floating particulates and a second PEG step was performed by adding PEG to a final concentration of 12% (the supernatants were assumed to contain 3.5% PEG). After a second centrifugation, the supernatants were discarded and the IgY pellets were resuspended in PBS at approximately ⅙ the original yolk volume. IgYs extracted from eggs from unimmunized hens (designated preimmune IgY) served as control IgY. The concentration of the fractionated IgY's were estimated by measuring the absorbance at 280 nm (an optical density at 280 nm of 1.3 equals 1 mg of IgY/ml. The antibody concentrations were about 25-30 mg/ml.

(c) Detection of anti-cytokine antibodies in the purified IgY preparations. In order to determine if anti-cytokine response was generated and to determine relative levels of the response, enzyme-linked immunosorbent assays (ELISA) were performed. Briefly, ninety-six well Falcon Pro-bind micro-titer plates were coated overnight at 4° C. with 100 µl/well of cytokine at 0.1-1.0 µg/ml PBS. The wells are then blocked with PBS containing 1-3% BSA and 0.05% Tween 20 and incubated for about 1 hour at 37 deg C. The blocking solution was removed and the immune or preimmune IgY was diluted in PBS containing BSA and the plates were incubated for 1 hour at 37 deg C. The plates were washed 3 times with PBS containing 0.05% Tween 20 and three times with PBS alone. Alkaline phosphatase-conjugated anti-chicken IgG was diluted 1:1000 in PBS containing 1% BSA and 0.05% Tween 20, added to the plates and incubated 1 hour at 37 deg C. The plates were washed as above and p-nitrophenyl phosphate at 1 mg/ml in 0.05 M $Na_2CO_3$, pH 9.5, 10 mM $MgCl_2$ was added. The plates were read in a Dynatech plate reader at 410 nm about 30 minutes after substrate addition. Good antibody titers (reciprocal of the highest immune IgY generating a signal about 3-fold higher than that of pre-immune) ranging from 10,000 to 50,000 was generated in all the cytokines except IL-1B which did not elicit an antibody response using the amounts of antigen used to immunize the hens. The level of antibody response in the hens against most of the cytokines considering the low amounts of antigen used for immunization indicate that mammalian cytokines are very immunogenic in the hens and is a well-suited system to generate mammalian cytokine antibodies.

Example 2

Neutralization of the In Vivo Effects of Endotoxin/D-GalN By Avian Anti-TNFα Antibody Endotoxin (LPS) can trigger a lethal reaction in vivo. In order to determine whether avian anti-TNF antibody is capable of neutralizing the lethal effects of endotoxin, a well-characterized and accepted murine model of endotoxic shock was utilized. [C. Galanos et al., *Proc. Natl. Acad. Sci. USA* 76:5939-5943 (1979).] The example involved: (a) use of a lethal dose of endotoxin in galactosamine (D-GalN)-sensitized mice; (b) neutralization of endotoxin lethality by premixture with avian anti-TNF antibody; and (c) rescue of lethality by administration of avian anti-TNF antibody at time points subsequent to LPS administration.

(a) A lethal dose (10-100 ng) of endotoxin in galactosamine-sensitized mice was administered to C3H/HEN (Charles River, Wilmington, Mass.) mice that were co administered 18 mg of D-galactosamine-HCl in 200 µl of phosphate buffered saline (PBS). The latter compound is a specific hepatotoxic agent that increases the sensitivity of experimental animals to endotoxin several thousand-fold. [C. Galanos et al., *Proc. Natl. Acad. Sci. USA* 76:5939-5943 (1979).] To accomplish this determination, *E. coli* 0111:B4 LPS (List Biological Laboratories, Campbell, Calif.) in PBS was injected intraperitoneally, along with 18 mg of D-galactosamine (Sigma Corp.).

(b) Neutralization of endotoxin lethality by premixture with chicken anti-TNF antibody was performed mixing 10-100 ng of *E. coli* 0111:B4 LPS with 4-8 mg of polyclonal anti-TNF antibody (prepared as described in Example 1). The results are shown in Table 1. Note that the use of anti-TNF antibody premixed with endotoxin resulted in a significant reduction in the lethality as compared to PBS and Preimmune premix controls, with a 76% survival rate for the anti-TNF antibody premix contrasted with 0% survival rates for both the PBS and Preimmune premix controls.

(c) Rescue of lethality by administration of chicken anti-TNF antibody was attempted at time points subsequent to LPS administration. Survival was assessed at 5, 10, 30 and 60 minutes post induced shock. The results are shown in Table 1, which describes the use of avian anti-TNF of the present invention, as administered at various temporal intervals to mice that had been induced with septic shock syndrome. Note that the shock-induced mice which were treated with the avian anti-TNF antibody experienced a significant survival rate of 61% for a period up to 30 minutes post-shock. The anti-TNF survival rate of 20% at 60 minutes post shock further displays a low rate of lethality as compared with the 0% survival rates for both the PBS and Preimmune premix controls.

The results of this experiment demonstrates that avian anti-TNF antibody neutralizes the lethal effect of endotoxin in vivo and suggest that avian anti-TNF antibody will be useful in preventing sepsis as well as in treating the early stages of sepsis due to gram-negative bacteria.

TABLE 1

| Treatment | No. Of Expt. | No. Of Survivors/ No. Tested | % Survival |
|---|---|---|---|
| PBS (premix) | 2 | 0/7 | 0 |
| Preimmune (premix) | 4 | 0/20 | 0 |
| Anti-TNF (premix) | 3 | 13/17 | 76 |
| Anti-TNF (5 min. post) | 2 | 5/10 | 50 |
| Anti-TNF (10 min. post) | 1 | 3/5 | 60 |
| Anti-TNF (30 min. post) | 3 | 8/13 | 61 |
| Anti-TNF (60 min. post) | 2 | 2/10 | 20 |

Example 3

Neutralization of the In Vivo Effects Of Endotoxin/D-GalN by Avian Anti-TNF Antibody and Anti-IL-6 Antibody Administered in Combination As mentioned earlier, LPS can trigger a lethal reaction in vivo. In order to determine whether an avian anti-TNF antibody in combination with another anti-cytokine antibody can increase the survival rate post-challenge beyond that of anti-TNF antibody alone, several combination therapies were tested. The combination therapies were tested in a well-characterized and accepted murine model of endotoxic shock using LPS and galactosamine. [C. Galanos et al., *Proc. Natl. Acad. Sci. USA* 76:5939-5943 (1979).] The example involved: (a) use of a lethal dose of endotoxin in galactosamine-sensitized mice; and (b) rescue of lethality by administration of anti-TNF antibody in combination with anti-IL-6 antibody at time points subsequent to LPS administration.

(a) A lethal dose of endotoxin in galactosamine-sensitized mice was administered according to the method referred to in Example 2 part (a) above. Again, 10-100 ng of LPS with 18 mg of DGalN was an effective lethal dose in 20-22 g C3H/HEN mice.

(b) Rescue of lethality by administration of anti-TNF antibody in combination with anti-IL-6 antibody was attempted at various time points subsequent to LPS/D-GalN administration. In these experiments 4-8 mgs of antibody in PBS were administered i.p. When using the anti-TNF antibody/anti-IL6 antibody combination therapy, the antibodies were mixed at a 1:1 ratio and half the amount of each individual antibody was used (i.e., as compared to the treatments where each antibody is used alone). Survival was assessed at 60, 120, 180 and 240 minutes after the induced shock.

The results are shown in Table 2, which shows the results following the use of the avian anti-TNF antibody and anti-IL-6 antibody combination of the present invention, as administered to shock-induced mice at various temporal intervals. Of particularly note are the percentage of survivors (82%) for the avian anti-TNF and anti-IL6 combination administered at 60 minutes post shock, as contrasted with the significantly lower survivor numbers (25%) for the Preimmune premix controls at 60 minutes post shock. Significantly, anti-TNF, or anti-IL-6 administered alone at 60 minutes post shock showed only a 40% survival rate. Of further note is the fact that the avian anti-TNF and anti-IL6 combination survivors administered with the anti-TNF and anti-IL6 combination (indicated as "Combo") at 120 minutes after the onset of the of the septic reaction still showed significant survival rates of 48%, when compared with the preimmune control of 18% and 25% at 60 and 120 minutes post shock, respectively.

TABLE 2

| Treatment | No. Of Expt. | No. Of Survivors/ No. Tested | % Survival |
|---|---|---|---|
| PBS | 4 | 5/23 | 22 |
| Preimmune (60 min. post) | 2 | 2/11 | 18 |
| Preimmune (120 min. post) | 1 | 2/8 | 25 |
| Anti-TNF (60 min. post) | 1 | 2/5 | 40 |
| Anti-IL-6 (60 min. post) | 1 | 2/5 | 40 |
| Combo (60 min. post) | 4 | 18/22 | 82 |
| Combo (120 min. post) | 5 | 15/31 | 48 |
| Combo (180 min. post) | 1 | 2/6 | 33 |
| Combo (240 min. post) | 1 | 2/8 | 25 |

The results indicate that the protection afforded by the combination therapy begins to wane at 180 to 240 minutes post-challenge. Clearly, the results of this experiment demonstrate that avian anti-TNF antibody administered in combination with anti-IL-6 antibody can rescue mammals from the lethal effect of endotoxin in vivo, and is more effective in treating sepsis post-challenge than anti-TNF antibody alone. These results also suggest that an avian anti-TNF antibody and anti-IL-6 combination therapy will be useful in preventing or treating sepsis in the later stages of development in mammals, including but not limited to humans.

Example 4

Failure to Neutralize the In Vivo Effects Of Endotoxin by using Combinations of Anti-Gamma IFN and Anti-IL-6, or Anti-Gamma IFN and Anti-TNF In the above examples, a composition comprising a combination of polyclonal antibodies directed to TNF and IL-6 was shown to be capable of blocking the downstream cascade of sepsis in an animal model. In this example, other anti-cytokine IgYs were tested: (a) a polyclonal antibody against gamma IFN; (b) a combination of polyclonal antibodies directed to gamma IFN and IL-6; and (c) a combination of polyclonal antibodies directed to gamma IFN and TNF. Again, the LPS/D-GalN animal model was employed as described in Examples 2 and 3. The model was tested in the manner above (i.e, in an attempt to rescue animals post-induced shock). The results are shown in Table 3.

TABLE 3

| Treatment | No. Of Expt. | No. Of Survivors/ No. Tested | % Survival |
|---|---|---|---|
| Preimmune (60 min. post) | 2 | 2/11 | 18 |
| Anti-Gamma IFN (60 min. post) | 1 | 0/3 | 0 |
| Anti-Gamma IFN + Anti-IL-6 (60 min. post) | 1 | 1/3 | 33 |
| Anti-TNF + Anti-Gamma IFN (60 min. post) | 1 | 0/3 | 0 |

The results from Table 3 show that anti-gamma IFN antibody alone as well as combinations of this antibody with 1) antibodies to IL-6, and 2) antibodies to TNF, are unable to provide significant protection in the mouse 60 minutes post-challenge. In contrast to the anti-TNF/anti-IL-6 combination therapy, the anti-IFN combination therapies (tested in this example) do not appear to be capable of blocking the downstream cascade.

Example 5

Prevention of the In Vivo Effects of Endotoxin by Pretreatment

The anti-cytokine antibodies either singly or in combination were tested in another type of endotoxin shock model. This model uses only very high levels of LPS without D-Gal-N. This model is thought to be distinct from the LPS/D-Gal-N shock model in that cytokine antibodies effective in this model are ineffective in the other models. This model is also considered very aggressive, and the onset of septic shock is quite rapid. The example involved: (a) use of lethal doses of LPS in the mice; (b) neutralization of endotoxin lethality by a pretreatment or premixture with avian anti-TNF alpha antibody, anti-Gamma INF, and anti-IL-6; and (c) rescue of lethality by administration of combination therapy of avian anti-TNF alpha antibody, anti-Gamma INF, and anti-IL-6 post LPS challenge.

(a) A lethal dose of 1.2 mg of LPS (*Salmonella enteritidis*) (Sigma Chemical Co., St. Louis, Mo.) was administered intraperitoneally to 18-20 g C57BL/6 mice (Charles River) in 400 ml of PBS. This LPS only endotoxin shock model is described in J. Rothe et al. [*Nature* 364:798-802 (1993)].

(b) Neutralization of endotoxin lethality by a pretreatment with cytokine antibody was performed by intraperitoneally injecting 400 ml PBS containing 1.2 mg of LPS 1 hour later. In the premix studies the same amounts of cytokine antibody and LPS were premixed then immediately administered intraperitoneally. The results are shown in Table 4. Preimmune IgY was found to be ineffective in protecting the mice. In addition, pretreatment with anti-IL-12 was also ineffective. In contrast, anti-TNF and anti-gamma IFN as a pretreatment were very effective in protecting the animals with survival rates of 88% and 100%, respectively. Moreover, anti-TNF, anti-IL-6 and anti-gamma IFN as a premix were also effective, with survival rate of 77% and 88%.

TABLE 4

| Treatment | No. Of Expt. | No. Of Survivors/ No. Tested | % Survival |
| --- | --- | --- | --- |
| Preimmune (60 min. pretreatment) | 3 | 1/11 | 9 |
| Anti-TNF (60 min. pretreatment) | 2 | 7/8 | 88 |
| Anti-IL-12 (60 min. pretreatment) | 1 | 1/3 | 33 |
| Anti-Gamma IFN (60 min. pretreatment) | 1 | 3/3 | 100 |
| Preimmune (premix) | 2 | 0/6 | 0 |
| Anti-TNF (premix) | 2 | 3/6 | 50 |
| Anti-IL-6 (premix) | 3 | 7/9 | 77 |
| Anti-Gamma IFN (premix) | 3 | 8/9 | 88 |

(c) The rescue of lethality post LPS challenge using cytokine antibodies either singly or in combination is shown in Table 5. In all anti cytokine therapies shown in Table 5, the final amount of IgY administered to the mice was the same (4-8 mg). The combination therapies were comprised of ½ or ⅓ of each individual anti-cytokine in the dual therapies or the triple therapies respectively. PBS at 5 minute post challenge or preimmune at 5 and 10 minute post challenge were, as expected, unable to protect the mice. In addition, either anti-TNF alone at 5 and 15 minute post challenge or combination therapies of anti-IL-6/Gamma IFN (5 minute post) or anti-TNF/anti-IL-6 (5 and 15 minute post) could not significantly protect the animals. Interestingly, a triple combination of anti-TNF/anti-IL-6/anti-Gamma INF was completely effective at 5 minute post challenge but not at 15 minute post challenge.

These results indicate in this model anti-Gamma IFN may be beneficial in addition to anti-TNFα and anti-IL-6 combination found to be effective in the LPS/D-GalN shock model.

TABLE 5

| Treatment | No. Of Expt. | No. Of Survivors/ No. Tested | % Survival |
| --- | --- | --- | --- |
| PBS (5 min. post) | 1 | 0/4 | 0 |
| Preimmune (5 and 15 min. post) | 3 | 0/12 | 0 |
| Anti-TNF (5 and 15 min. post) | 2 | 0/9 | 0 |
| Anti-IL-6/Gamma IFN (5 min. post) | 1 | 1/3 | 33 |
| Anti-TNF/Anti-IL-6/Anti-Gamma IFN (5 min. post) | 2 | 6/6 | 100 |
| Anti-TNF/Anti-IL-6/Anti-Gamma IFN (15 min. post) | 1 | 1/3 | 33 |
| Anti-TNF/Anti-IL-6 | 2 | 0/9 | 0 |

*Survival at least 24 hours post-challenge (5 and 15 min. post).

Example 6

Neutralization of the In Vivo Effects of Endotoxin in a Gram-Positive Model

In the above examples, the combination of polyclonal antibodies directed to TNF and IL-6 was shown to be capable of blocking the downstream cascade of sepsis in an animal model involving gram negative sepsis. In this example, polyclonal antibodies directed to TNF were tested alone using a gram positive sepsis model. The gram-positive sepsis model was performed as described by S. Q. DeJoy et al., *J. Infect. Dis.* 169:150-156 (1994). To carry out tests on the model, 20-22 g C3H/HeN (Charles River) mice were treated i.p. with heat-killed *Staph. aureus* bacteria in the presence of galactosamine. The mice were given 0.1 ml of the killed bacteria at the optical density at $A_{600}$ of 90-100 mixed with 0.1 ml PBS with 18 mg of galactosamine. The mice are given i.p. 400 ul of PBS containing 4-8 mgs of IgY. IgY. The results (using the premix treatment format described in Example 2) are shown in Table 6.

TABLE 6

| Treatment | No. Of Expt. | No. Of Survivors/ No. Tested | % Survival |
| --- | --- | --- | --- |
| Untreated | 1 | 0/3 | 0 |
| Preimmune (premix) | 1 | 0/3 | 0 |
| Anti-TNF (premix) | 1 | 3/4 | 75 |

The results show that using anti-TNF antibody provided significant protection. The results of the post-challenge treatment are shown in Table 7. Both preimmune and anti-IL-6 antibody administered alone 5 minutes post-challenge were unable to protect the animals (i.e., survival rates were 20-25%). On the other hand anti-TNF antibody showed better protection, with the combination ("Combo") therapy (using equal amounts of anti-TNF antibody and anti-IL-6 antibody) gave the best survival rates at 89% (at 48 hours post-challenge). These results indicate that an anti-cytokine combination therapy (in accordance with the teachings of the present invention) against gram-positive sepsis is an effective treatment.

TABLE 7

| Treatment | No. Of Expt. | No. Of Survivors/ No. Tested | % Survival |
| --- | --- | --- | --- |
| Preimmune (5 min. post) | 2 | 1/5 | 20 |
| Anti-IL-6 (5 min. post) | 2 | 2/8 | 25 |
| Anti-TNF (5 min. post) | 2 | 4/8 | 50 |
| Combo (5 min. post) | 2 | 8/9 | 89 |

I claim:

1. A therapeutic composition for use with a mammal having a plurality of symptoms of sepsis, wherein said symptoms comprise arterial hypotension and at least one selected from the group consisting of metabolic acidosis, fever, decreased systemic vascular resistance, tachypnea, and organ failure, said therapeutic composition comprising avian anti-TNF-alpha, anti-IL-6, and anti-IFN-gamma antibodies.

2. A method of treatment, comprising:
   a) providing:
      i) a mammal having sepsis,
      ii) a therapeutic preparation, comprising anti-TNF-alpha, anti-IL-6, and anti-IFN-gamma antibodies; and
   b) administering said preparation to said mammal wherein said sepsis is reduced.

3. The method of claim 2, wherein said antibodies are polyclonal.

4. A therapeutic composition for use with a mammal having sepsis, said therapeutic composition comprising avian anti-TNF-alpha, anti-IL-6, and anti-IFN-gamma antibodies.

5. A method of treatment, comprising:
   a) providing:
      i) a mammal having septic shock,
      ii) a therapeutic preparation, comprising anti-TNF-alpha, anti-IL-6, and anti-IFN-gamma antibodies; and
   b) administering said preparation to said mammal wherein said septic shock is reduced.

6. The method of claim 5, wherein said antibodies are polyclonal.

7. A therapeutic composition for use with a mammal having septic shock, said therapeutic composition comprising avian anti-TNF-alpha, anti-IL-6, and anti-IFN-gamma antibodies.

* * * * *